United States Patent [19]

Skonezny et al.

[11] Patent Number: 5,539,099
[45] Date of Patent: Jul. 23, 1996

[54] PROCESS FOR LARGE-SCALE PREPARATION OF 2',3'-DIDEHYDRO-2',3'-DIDEOXYNUCLEOSIDES

[75] Inventors: Paul M. Skonezny, Cicero; Emerich Eisenreich, Manilus; Derron R. Stark, Syracuse, all of N.Y.; Brenda T. Boyhan, Edison, N.J.; Stephen R. Baker, Cicero, N.Y.

[73] Assignee: Bristol-Myers Squibb Company, New York, N.Y.

[21] Appl. No.: 309,636

[22] Filed: Sep. 23, 1994

Related U.S. Application Data

[63] Continuation-in-part of Ser. No. 152,155, Nov. 15, 1993, abandoned, and Ser. No. 152,778, Nov. 15, 1993, abandoned.

[51] Int. Cl.$^6$ .............................. C07H 1/00; C07H 19/06
[52] U.S. Cl. .................... 536/28.2; 536/28.1; 536/28.53; 536/28.54
[58] Field of Search .............................. 536/28.2, 28.54, 536/28.1, 28.53

[56] References Cited

U.S. PATENT DOCUMENTS 4,904,770  2/1990  Starrett, Jr. et al. ................. 536/27.14

OTHER PUBLICATIONS

Xu et al., Tetrahedron Letters, vol. 32, No. 24, pp. 2817–2820 (1991).
Herwitz et al., *Synthetic Procedures in Nucleic Acid Chemistry*, vol. 1, 1968, p. 344.
Mansuri et al, *J. Med. Chem.*, 1989, p. 461.
Adachi et al, *Carbohydrate Research*, 1979, p. 113.
Cosford et al, *J. Org. Chem.*, 1991, p. 2161.

*Primary Examiner*—James O. Wilson
*Attorney, Agent, or Firm*—Richard P. Ryan

[57] ABSTRACT

An improved process suitable for large-scale production of 2',3'-didehydro-3'-deoxythymidine (d4T) and close analogs is disclosed. The improved process yields d4T in high yield and purity without the use of hazardous reactions or reagents and incorporates several process improvements important on a large scale including a novel purification step involving the isolation of a d4T.N-methylpyrrolidinone solvate.

13 Claims, No Drawings

5,539,099

PROCESS FOR LARGE-SCALE PREPARATION OF 2',3'-DIDEHYDRO-2',3'-DIDEOXYNUCLEOSIDES

CROSS-REFERENCE TO RELATED APPLICATIONS

This is a continuation-in-part application of U.S. Ser. No. 08/152,155, filed Nov. 15, 1993, now abandoned, combined with U.S. Ser. No. 08/152,778 also filed Nov. 15, 1993, now abandoned.

BACKGROUND OF THE INVENTION

The present invention concerns an improved process for producing certain didehydro-dideoxynucleosides such as 2',3'-didehydro-3'-deoxythymidine (d4T) that is suitable for adaptation to large-scale manufacture.

There have been several processes reported for synthesizing 2',3'-didehydro-2',3'-dideoxynucleosides such as d4T. Most proceed via an anhydronucleosidic intermediate.

The nucleoside derivative, 2',3'-didehydro-3'-deoxythymidine (d4T), has previously been prepared by various synthetic processes. Horwitz et al, in *Synthetic Procedures in Nucleic Acid Chemistry* (Vol. 1), Zorbach et al (eds); Interscience, New York, p. 344, describe the process of Route 1 (below), which utilizes 3',5'-anhydrothymidine as the starting material, and employs flammable and moisture sensitive potassium tertiary butoxide (KOt-Bu) in dimethyl sulfoxide (DMSO). Besides the material handling difficulties, the process is impractical on a large scale due to decomposition of the product during its isolation from a DMSO solution, when it is subjected to the required high temperatures and strongly basic conditions for extended periods.

ROUTE 1

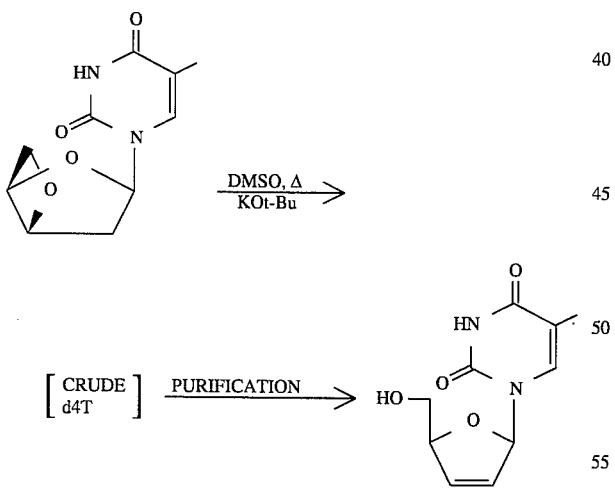

An improvement in isolation noted by Mansuri et al in *J. Med. Chem.*, 1989, 461 (Route 2), gives the potassium salt of d4T as an oily solid by dilution of the DMSO reaction mixture with toluene before further processing. However, on a large scale, the volumes used are unmanageable and generate large amounts of waste solvents, which are difficult to recover. Also, the isolated salt is very sensitive to moisture and excessive drying. After redissolution and neutralization, crude d4T is isolated and dried and a further reslurry in solvent is necessary to obtain the final product.

ROUTE 2

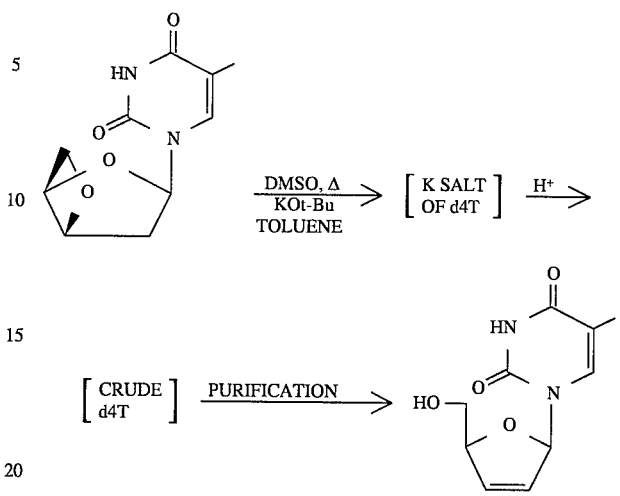

Starrett, Jr. et al in U.S. Pat. No. 4,904,770 disclosed modification of the Mansuri process that comprised room temperature reaction of the 3',5'anhydro intermediate with the strong base in a polar organic solvent, e.g. KOt-Bu/DMSO followed by trituration of the resulting potassium salt of the 2',3'-didehydro-2',3'-dideoxynucleoside in an organic solvent, e.g. cold toluene. After redissolution and neutralization, crude d4T is obtained by acetone extraction of the solids isolated from the neutralization process.

A different approach to minimizing the product decomposition problem involved replacement of the KOt-Bu/DMSO system.

This variation (Route 3), using hexamethylphosphoric triamide (HMPA) and sodium hydroxide, eliminated the decomposition problems in the above Routes 1 and 2, since the HMPA solvent could be removed from an aqueous solution as a chloroform complex. However, the use of highly toxic agents that are reputed carcinogens as well, such as HMPA and chloroform, is hazardous on a large scale and is to be avoided. This process is disclosed in Adachi, et al, *Carbohydrate Research*, 1979, 113.

ROUTE 3

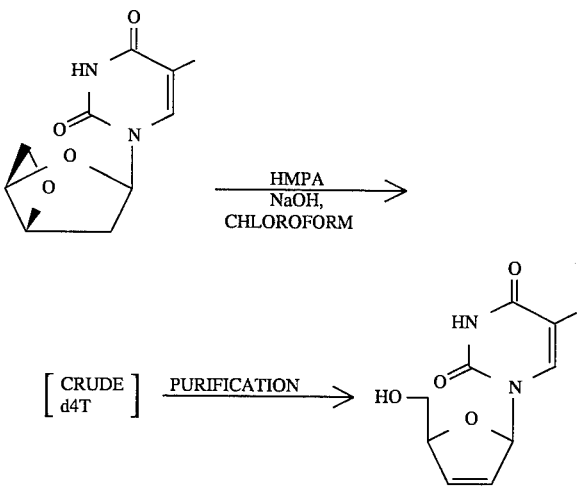

Cosford et al, in *J. Org. Chem.*, 1991, 2161, disclose a less closely related route (Route 4) using a tritylated phenylselenyl thymidine derivative. The generation of highly toxic selenium wastes and the chromatography required are undesirable, especially on a large scale.

ROUTE 4

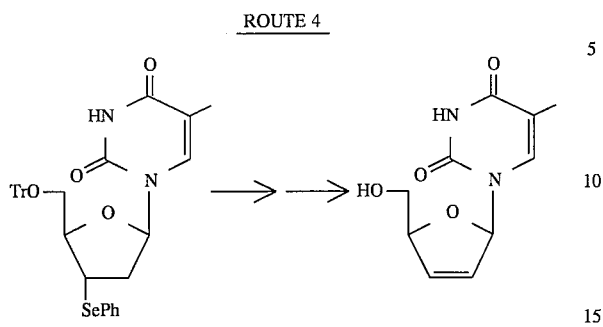

SUMMARY OF THE INVENTION

This invention is an improved process for producing 2',3'-dideoxy-2',3'-didehydronucleosides, in particular d4T, on a large scale in high yield and purity. The instant process incorporates various improvements in the selection, handling, processing and purification of reactants, intermediates, and products that result in making the process particularly useful for large-scale manufacture of a product such as d4T.

DETAILED DESCRIPTION OF THE INVENTION

In its broadest generic aspect, the invention is an improved process, amenable to large-scale manufacture, for producing a 2',3'-dideoxy-2',3'-didehydronucleoside represented by the formula

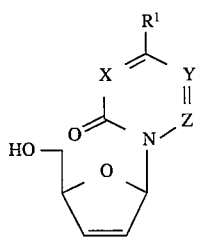

wherein the base moiety is a member selected from the group of unsubstituted and substituted bases consisting of pyrimidine, aza-pyrimidine, and deaza-pyrimidine. Specifically, X is selected from N and C-H; Y is selected from $C-R^2$ and N; Z is selected from C-H and N; $R^1$ is selected from OH and $NH_2$; and $R^2$ is selected from H, unsubstituted and halo-substituted alkyl having the formula $C_nH_{2n}A$, and alkenyl having the formula $-(CH_2)_m-CH=CHA$ wherein m is an integer selected from 0, 1, 2 and 3, n is an integer selected from 1, 2, and 3 and A is selected from H, F, Cl, Br, and I, comprising the steps of:

(a) converting a 2'-deoxynucleoside represented by the formula

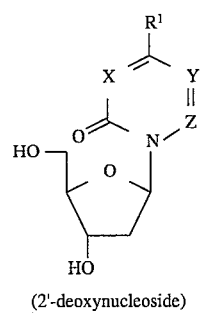

(2'-deoxynucleoside)

to a reactive 3',5'-anhydro-2'-deoxynucleoside intermediate represented by the formula

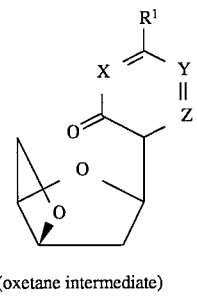

(oxetane intermediate)

and (b) converting the reactive (oxetane intermediate) 3',5'-anhydro-2'-deoxynucleoside, from step (a) above, in the presence of strong base, to a 2',3'-dideoxy-2',3'-didehydronucleoside. Improvement in this process comprising:

use of a polar solvent such as acetone in the mesylation reaction of the 2'-deoxynucleoside leading to preparation of the 3',5'-di-O-mesylthymidine in step (a);

use of an organic base having a pka between 5.5 and 8.0 in the mesylation reaction in step (a);

use of alcoholic hydroxide in step (b);

use of N-methylpyrrolidinone to form a solvate of the dideoxy-didehydronucleoside for ease of isolation and purification.

In a more narrow aspect, the invention relates to the production of d4T in high yield via a process that can be adapted to large-scale manufacture of d4T.

The d4T process comprises:

(a) the production of 3',5'-di-O-mesylthymidine from thymidine and mesyl chloride, improvements in the step comprising use of a polar solvent, preferably acetone and about 2 to 4 equivalents of an organic base stronger than pyridine but weaker than triethylamine, preferably N-methylmorpholine;

(b) the production of 3',5'-anhydrothymidine by treating 3',5' -di-O-mesylthymidine with aqueous hydroxide;

(c) the production of d4T from 3',5'-anhydrothymidine, where the improvement in terms of large-scale production comprises the heating of a mixture of 3',5'-anhydrothymidine and hydroxide, preferably potassium hydroxide, in an alcohol, preferably isopropanol; and (d) an improved isolation/purification process that comprises isolating the product as its N-methylpyrrolidinone (NMPO) solvate, then decomposing the solvate by heating in isopropanol to give d4T in high yield and purity.

The improved synthetic process of d4T allowing efficient scale-up is outlined in Scheme A. The present invention also goes to the production of d4T from 3',5'-anhydrothymidine (III) and the isolation and purification of product via the d4T.NMPO solvate (II) as separable and discrete processes in themselves.

Scheme A
Improved Process for Large-Scale Production of D4T

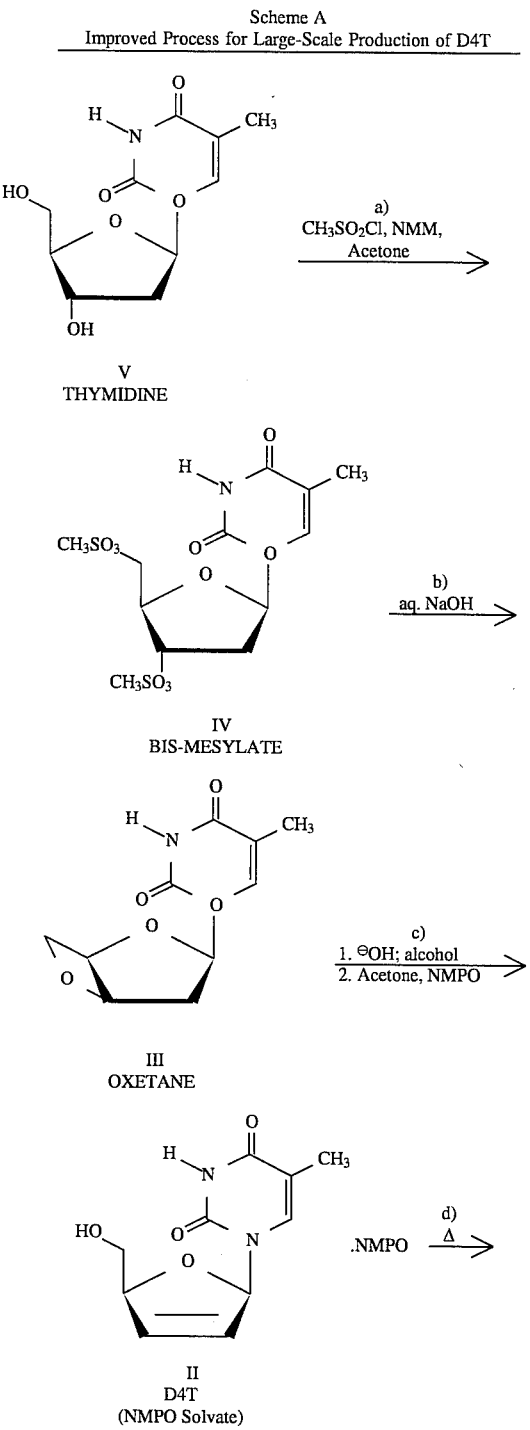

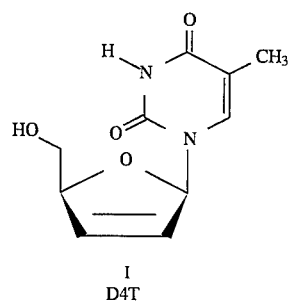

I
D4T

-continued
Scheme A
Improved Process for Large-Scale Production of D4T

The initial reaction of Scheme A, denoted a), involves the mesylation of the 3'and 5'-hydroxy groups of thymidine (V). Improvement of this step involves the selection of solvent and organic base. Useful solvents for step a) are acetonitrile, DMF and, preferably, acetone. Useful organic bases are those such as the picolines, the lutidines, and preferably N-methylmorpholine (NMM)—all of which have pka values between 5.5 and 8.0, i.e. bases stronger than pyridine but weaker than triethylamine. The reaction proceeds at temperatures from about 20° to 50° C., preferably about 30° to 40° C. with reaction times from about 0.5 hour to 2 hours and preferably for about 1 hour. Previous syntheses of the bis-mesylate (IV) utilized pyridine as a basic solvent. These syntheses generated large waste streams of pyridine, required longer reaction times and required recrystallization of (IV) before further use.

The bis-mesylate (IV) is heated with aqueous hydroxide, sodium hydroxide being preferred, at about 50° to 100° C. for about 2 to 8 hours (in step b). Preferred conditions are to heat at about 75° to 85° C. from about 3 to 5 hours. Neutralization is effected with an inorganic acid such as HCl to give the 3',5'-anhydrothymidine (oxetane, III).

Steps (c) and (d) are major contributors to the improved d4T process. The use of alcoholic KOH in (c) and formation of the solvate (II) bring about large improvement. As shown, the 3',5'-anhydrothymidine (III) is heated in alcoholic potassium hydroxide, isopropanol being a preferred choice, to produce crude d4T in step (c). Of surprise is the stability of d4T in the hot, caustic alcoholic environment of this process step. After neutralization with an inorganic acid, such as hydrochloric acid, the alcohol is removed by distillation and the resulting mixture is filtered to remove insoluble materials. The filtrate is then treated with N-methylpyrrolidinone and an aprotic ester, amide or ketone solvent, with acetone and butyl acetate being preferred, at about 30° to 60° C., preferably about 50° C. The mixture is cooled to the range of from −10° C. to 10° C. and the solid d4T.NMPO solvate (II) is isolated by filtration, leaving difficult-to-remove contaminants in the filtrate. Gentle refluxing of the solvate in alcohol for a period of time from 0.5 to 2 hours provides d4T in high yield and purity.

This improved process offers advantages, not only in yield and purity of product, but in adaptability for large-scale production due to the process steps utilized and the reagents and reaction conditions employed. It is well appreciated by those skilled in large-scale organic chemical manufacture that many processes, procedures, and/or reactions are not amenable to being carried out on a large scale as is done in a pilot plant or a manufacturing facility. Typical scale-up problems involve processes that involve the use of hazardous or toxic reagents and solvents; highly exothermic or endothermic reactions, high pressure or high vacuum processes such as those required for certain high pressure reactions or high vacuum distillations. Purification procedures requiring large amounts of solvent and fractional crystallization or chromatographic separations are also problematic for large-scale operation. Further, many processes, for a variety of reasons, give reduced product yields and/or increased by-products when subjected to scale-up. Recent emphasis on the prevention of toxic wastes and safe disposal of spent chemicals, as well as regulations limiting emissions and effluents, point up the additional costs where large-scale processes produce emissions and waste products that must be safety handled and disposed of.

Previous processes for producing d4T have not been particularly amenable to scale-up for many of the reasons listed above as well as other process problems arising from and unique to the reagents and reaction conditions employed. In contrast, the instant process provides the desired product in high yield and purity without the use or generation of toxic materials. The reaction times are reduced and the intermediate products are carried on in the synthetic scheme without further processing. Specifically, we have found that, unlike the results with previous processes, the d4T product is surprisingly stable to heating in alcoholic potassium hydroxide. The novel use of the d4T.NMPO solvate to effect purification, without requiring toxic materials or generating hazardous wastes, also contributes to the instant process's suitability for scale-up. Inefficiencies found in previous processes for d4T have been overcome by process modifications discovered and incorporated into the improved process of the present invention.

In sum, the new, improved process for producing d4T and related analogs is amenable to large-scale use by virtue of its selection of reagents, reaction conditions, and separation/ purification features that result in an efficient process minimizing troublesome impurities and product degradation as well as providing a high yield and purity of product without generation of wastes that are either toxic or produced in large volume.

DESCRIPTION OF SPECIFIC EMBODIMENTS

The improved process of this invention is illustrated in greater detail by the following examples directed to preferred embodiments of the process steps described supra. These examples should not be construed as limiting the scope of the present invention in any way.
A. COMPOUND IV

EXAMPLE 1

3',5'-Di-O-methanesulfonylthymidine

A five liter, three-necked, round bottom flask was equipped with an overhead stirrer and paddle, a 500 mL dropping funnel, a Claisen adapter with thermocouple probe and a reflux condenser. Thymidine (363.3 g, 1.5 moles) and N-methylmorpholine (508.3 g, 5.02 moles) were added to the flask with acetone (2.00 L). The mixture was stirred while adding methanesulfonyl chloride (498.3 g, 4.35 moles) slowly over about one hour, with cooling to maintain 30°–35° C. during the addition. An additional 1.50 L of acetone was added to the mixture to maintain adequate stirring. After the addition was complete, the mixture was stirred for 1 hour at 30°–35° C. The reaction was then transferred in portions to water (9.66 L) being stirred in a 20 L polyethylene tank. The pH of the aqueous slurry was adjusted with 12N HCl to pH 2.5 and stirred at ambient temperature for an additional two hours. The slurry was filtered and the solid was washed with water (2.9 L) and isopropanol (1.45 L). The solid was air dried overnight to give 564.6 g (94.5%) of the title compound which assays 97.1% (by weight) purity.

EXAMPLE 2

3', 5'-Di-O-methanesulfonylthymidine

To a dry, round-bottom flask purged with nitrogen was added thymidine (10.0 g, 0.0412 mole) and acetone (30 mL). The slurry was stirred and 3, 5-lutidine (17.7 g, 0.165 mole) was added. Then, methanesulfonyl chloride (13.8 g, 0.124 mole) was added over ten minutes with the temperature rising to 40° C. After 45 minutes, the reaction was complete and the thick slurry was diluted with 150 mL of water. The slurry was stirred for 25° C. for 30 minutes, and then cooled at 0°–5° C. for 30 minutes. The solids were collected, washed with water (80 mL) and isopropanol (40 mL), then dried to give 16.1 g (98.2%) of the title compound.
B. COMPOUND III

EXAMPLE 3

3', 5'-Anhydrothymidine

A two liter, four-necked flask was equipped with an overhead stirrer and paddle, a pH probe connected to an automatic titrator, and a thermocouple probe connected to a temperature controller and a heating mantle. Water (350 mL) was added to the flask and about a 20–25% portion of 3',5'-di-O-methanesulfonylthymidine (500 g total, 1.255 moles) was added with stirring. The pH was adjusted to 10.5 with 30% aq. sodium hydroxide and the temperature was raised to 50° C. While maintaining the temperature at 50°–55° C. and the pH at 10.5–11.0, the remaining 3',5'-di-O-methanesulfonylthymidine was added slowly as material dissolved, maintaining a stirrable slurry. A total of 502 g (3.765 moles) of 30% aq. NaOH is added. The reaction mixture is then heated at 70° C. for one hour, then cooled to 10°–15° C. The pH was adjusted to 9.7–9.8 with 12N HCl using cooling to maintain the temperature at 10°–15° C. while crystallization occurred. Finally, the slurry was adjusted to pH 6.0–6.5 with 12N HCl and cooled to 0°–5° C. and filtered. The collected solids were washed with cold (0°–5° C.) water (200 mL) and air dried to give 211.6 g (75.2%) of the title compound, which assays 99.8% (by weight) purity.
C. COMPOUND II

EXAMPLE 4

2',3'-Didehydro-3'-deoxythymidine N-methylpyrrolidinonesolvate (d4T.NMPO)

A five liter, three-necked flask was equipped with an overhead stirrer and paddle, a reflux condenser, a temperature probe, and a heating mantle. Isopropanol (1.25 L) and potassium hydroxide (198 g, 3.0 moles) were added to the flask and heated to 50° C. stirring. Then, 3', 5'-anhydrothymidine (168.2 g, 0.75 mole) was added portion-wise. The resulting solution was then heated at 78°–80° C. for 3.5 hours. The solution was cooled to 20°–25° C., diluted with isopropanol (1.75 L), then taken to pH 4–6 with concentrated HCl and cooled to 0° C. The precipitated KCl was filtered off and washed with isopropanol (200 mL). The combined filtrate and wash was divided into three equal portions. Each portion was mixed with N-methylpyrrolidinone (54 mL) and concentrated to a thick oil at 50° C./15–20 mm Hg, then diluted with acetone (120 mL) and warmed at 50° C. for 15 minutes. The mixture was then cooled to 15° C., forming a thick slurry. The solids were collected by filtration to give a total of 65.96 g (81.6%) of the title compound which assays 68.5% (by weight) d4T.

EXAMPLE 5

2',3'-Didehydro-3'-deoxythymidine N-methylpyrrolidinone solvate (d4T.NMPO)

Using the same equipment in Example 4, isopropanol (1.235 L) and potassium hydroxide (211.97 g, 3.211 moles) were added to the flask and heated to 50° C. while stirring. Then, 3',5'-anhydrothymidine (180.0 g, 0.803 mole) was added portion-wise. The resulting solution was then heated at 78°–80° C. for four hours. The solution was cooled to 20°–25° C., diluted with isopropanol (1.976 L), then taken to pH 5.6 with concentrated HCl and cooled to 10° C. The precipitated KCl was filtered off and washed with isopropanol (200 mL). The combined filtrate and wash was divided into two equal portions. The first portion was mixed with N-methylpyrrolidinone (90 mL) and concentrated to a thick oil at 50° C./15–20 mm Hg, then diluted with acetone (100 mL) and warmed to 50° C. for 15 minutes. The mixture was then cooled to <0° C., forming a thick slurry. The solids were collected by filtration to give 104.47 g (80.5%) of the title compound which assays 69.1% (by weight) d4T.

The second portion of the combined filtrate and wash was treated with the mother liquor from the first portion plus fresh NMPO (31 mL). Following the procedure described above, solids were collected to give 107.93 g (83%) of the title compound which assay 70.0%.

D. COMPOUND I(d4T)

EXAMPLE 6

2', 3'-Didehydro-3'-deoxythymidine (d4T)

A 1 L round-bottom flask with a stirrer was fitted with a reflux condenser and a heating mantle. d4T.NMPO (55.25, 0.27 mole) was added along with isopropanol (550 mL), Dicalite (filter aid, 5.5 g) and Darco KB (activated carbon, 5.5 g). The mixture was stirred and heated to reflux, filtered hot and the carbon cake was washed with hot isopropanol (165 mL). The combined filtrate and wash was concentrated by distillation to 200 mL and the product crystallized during slow cooling to ambient temperature. After cooling to 0° C., the solids were collected, washed with cold (0° C.) isopropanol (50 mL) and air dried to give 34.6 g (90.4%) of the title compound which assays 98% (by weight) purity.

Reasonable variations, such as those which would occur to one skilled in the art, can be made herein without departing from the scope of the invention.

E. SCALE-UP

The process has been scaled-up. On a scale of about 350 kg of V, step (a) proceeded in about 88.5% yield (based on activity) and step (b) similarly provided the oxetane intermediate (III) in about 75% yield. Isolation of the NMPO solvate (II) proceeds in about 76–89% yield and is converted in 90% yield into d4T product.

We claim:

1. The process for producing 2', 3'-didehydro-3'-deoxythymidine (d4T) comprising the steps of:

a) reacting thymidine (V) with mesyl chloride in the presence of an organic base selected from the group consisting of N-methyl-morpholine, the picolines, and the lutidines, to give 3', 5'-di-O-mesylthymidine (IV);

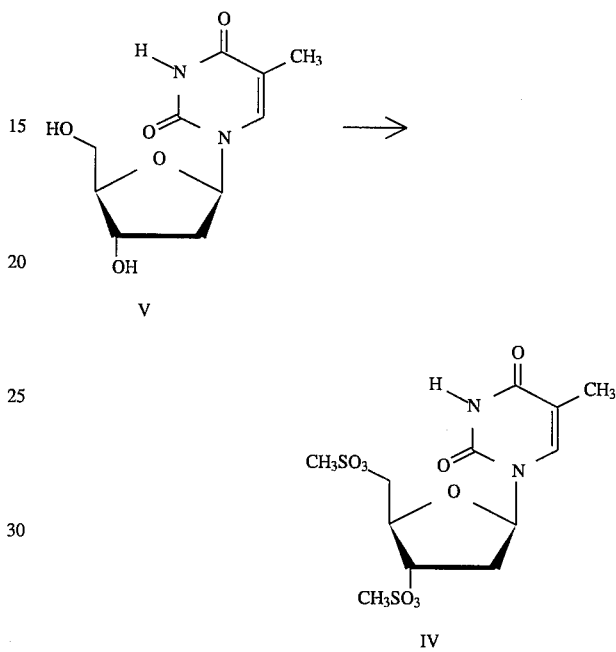

b) treatment of the bis-mesylate (IV) with aqueous hydroxide to form 3', 5'-anhydrothymidine (III);

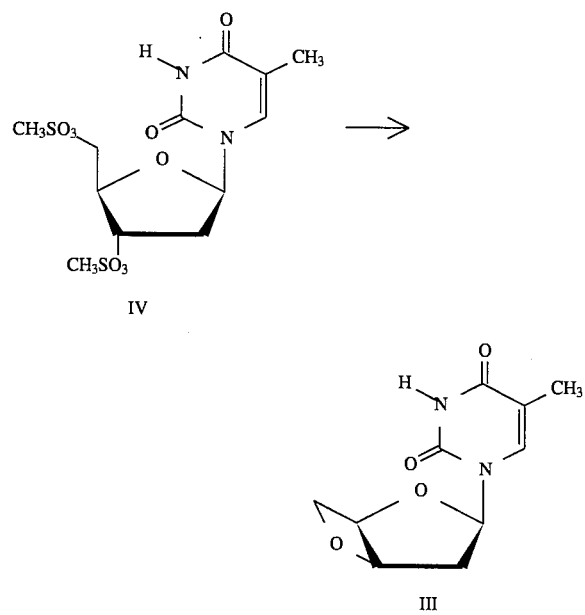

c) conversion of (III) into d4T.NMPO solvate (II) by heating (III) in alcoholic hydroxide and, after acid neutralization, treating the reaction mixture with N-methylpyrrolidinone and an aprotic ester, amide or ketone solvent to precipitate (II); and

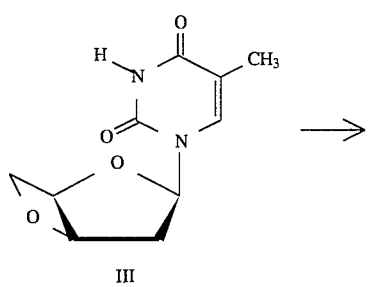

III

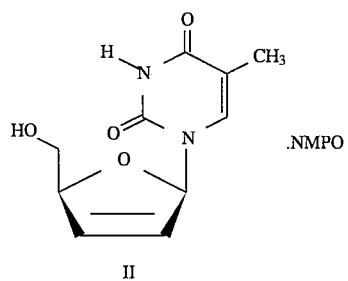

II d) heating the isolated d4T.NMPO solvate (II) in alcoholic solution to yield d4T (I) in high purity

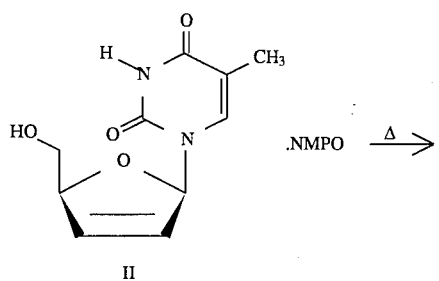

II

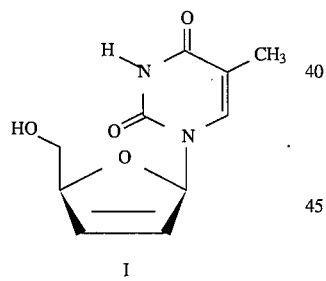

I

2. The process of claim 1 wherein the organic base in step (a) is N-methylmorpholine.

3. The process of claim 1 wherein the d4T.NMPO solvate (II) of step (c) is isolated by filtration from an acetone slurry.

4. The process of claim 1 wherein the d4T.NMPO solvate (II) is converted in step (d) to d4T (I) in isopropanol.

5. A process for isolating and purifying d4T comprising the formation and removal of the N-methylpyrrolidinone solvate of d4T from a process reaction mixture followed by generation of purified d4T by heating the isolated d4T.NMPO solvate in an alcoholic medium.

6. The process of claim 5 wherein the alcoholic medium is isopropanol.

7. The improved process for producing 2', 3'-didehydro-3'-deoxythymidine (d4T) from 3', 5'-anhydrothymidine comprising the steps of:

(a) heating 3', 5'-anhydrothymidine in alcoholic hydroxide;

(b) neutralizing with acid and removing the insoluble salts and alcohol;

(c) treating with N-methylpyrrolidinone and acetone to precipitate a d4T.NMPO solvate which is isolated from the process reaction mixture; and (d) heating the d4T.NMPO solvate in alcohol to produce d4T.

8. The process of claim 7 wherein the alcohol of step (a) is isopropanol.

9. The process of claim 7 wherein the d4T.NMPO solvate is isolated in step (c) by filtration from an acetone slurry.

10. The process of claim 7 wherein the alcohol of step (d) is isopropranol.

11. The d4T.NMPO solvate (II) of the formula

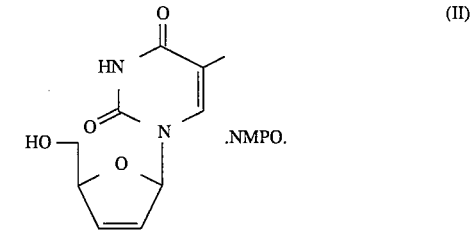

(II)

12. A process for isolation and purification of d4T that utilizes the isolation of the d4T.NMPO solvate (II) of claim 11 from a reaction mixture, followed by its conversion to d4T.

13. A process for producing d4T consisting of heating the isolated d4T.NMPO solvate (II) of claim 11 in alcohol.

* * * * *